(12) United States Patent
Ide (10) Patent No.: US 6,454,703 B1
(45) Date of Patent: Sep. 24, 2002

(54) ANGLE PORTION OF AN ENDOSCOPE (75) Inventor: Masao Ide, Omiya (JP)

(73) Assignee: Fuji Photo Optical Co., Ltd., Omiya (JP)

( * ) Notice: Subject to any disclaimer, the term of this patent is extended or adjusted under 35 U.S.C. 154(b) by 48 days.

(21) Appl. No.: 09/672,894

(22) Filed: Sep. 29, 2000

(30) Foreign Application Priority Data

Sep. 30, 1999 (JP) ............................................ 11-278190

(51) Int. Cl.$^7$ ................................................. A61B 1/00
(52) U.S. Cl. ...................................... 600/142; 600/146
(58) Field of Search ............................... 600/142, 146, 600/148, 152, 139

(56) References Cited

U.S. PATENT DOCUMENTS

| | | | | |
|---|---|---|---|---|
| 4,805,596 A | * | 2/1989 | Hatori ............................. | 128/4 |
| 5,025,804 A | * | 6/1991 | Kondo ............................ | 128/4 |
| 5,174,277 A | * | 12/1992 | Matsumaru ..................... | 128/4 |
| 5,897,488 A | * | 4/1999 | Ueda .......................... | 600/143 |
| 2001/0018552 A1 | * | 8/2001 | Akiba ......................... | 600/146 |
| 2001/0023313 A1 | * | 9/2001 | Ide .............................. | 600/142 |
| 2002/0026095 A1 | * | 2/2002 | Sakamoto .................... | 600/142 |

* cited by examiner

Primary Examiner—Denise L. Esquivel
Assistant Examiner—Marc Norman
(74) Attorney, Agent, or Firm—Oblon, Spivak, McClelland, Maier & Neustadt, P.C.

(57) ABSTRACT

Within a flexible angling joint tube which is connected to a rigid tip end section of an endoscopic insertion instrument and which is formed by connecting a predetermined number of angle rings successively and pivotally by the use of pivoting pins, a plural number of operating wires are passed in an axial direction via the respective pivoting pins. Fore ends of the operating wires are fixedly anchored at fixation points in boundary portions of the rigid tip end section and the flexible angling joint tube. An operating wire fixation point for at least one operating wire is shifted to an angular position in the circumferential direction from a normal position on an axial extension line from a row of pivoting pins. A wire guide pin is fixedly provided at least one of angle rings which are connected by the foremost pivoting pins to guide the one operating wire in such a way as to evade at least a top portion of the foremost pivoting pin as the one operating wire is pulled or pushed in the axial direction to bend the angling joint tube.

5 Claims, 8 Drawing Sheets

ANGLE PORTION OF AN ENDOSCOPE

BACKGROUND OF THE INVENTION

1. Field of the Art

This invention relates generally to endoscopic insertion instruments for medical use, and more particularly to a flexibly bendable, angling joint tube for use as an angle portion of endoscopic insertion instruments.

2. Prior Art

Figure 8:
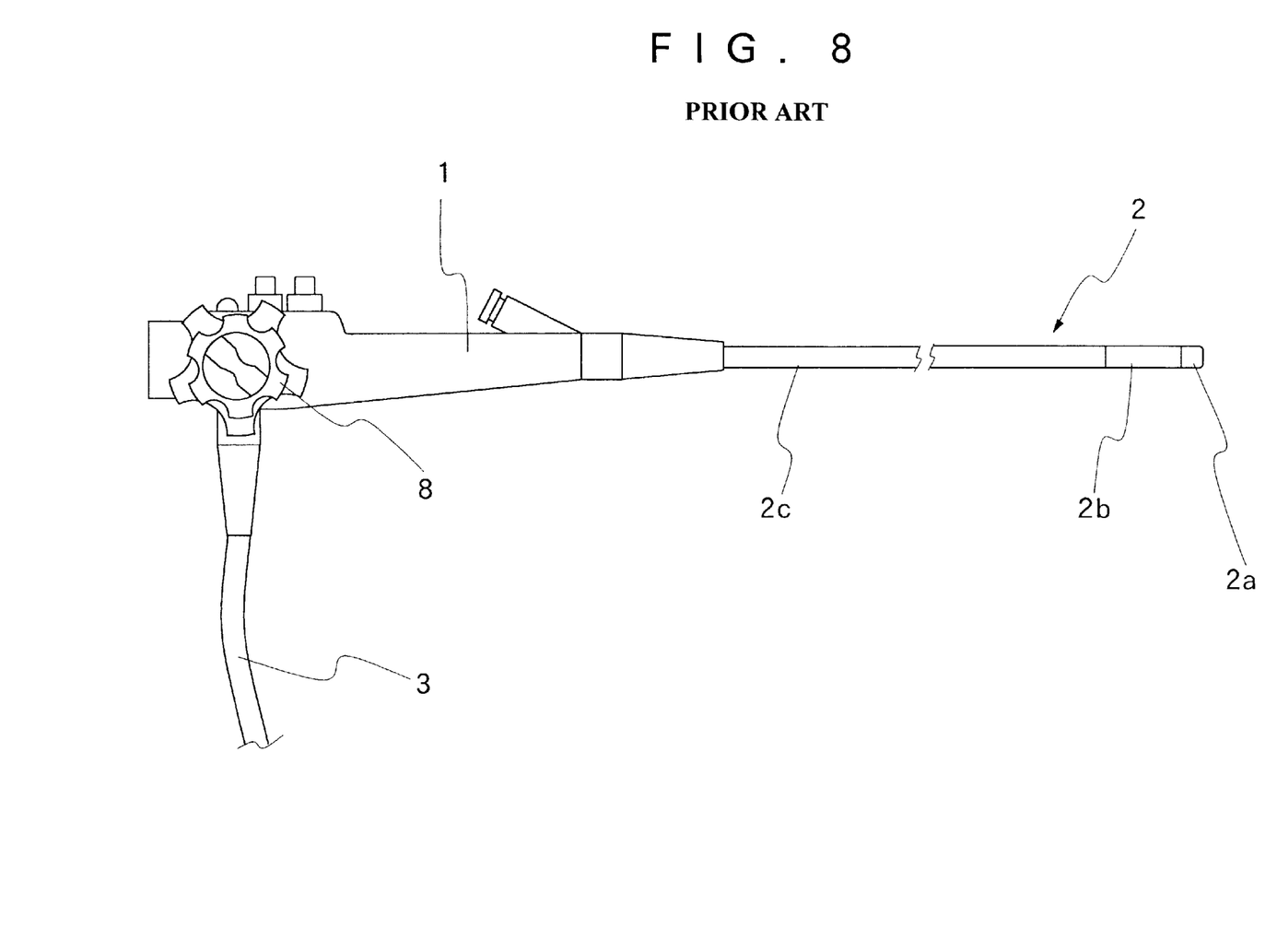
FIG. 8 is a schematic view of an endoscope, showing general layout of the endoscope.
Figure 9:
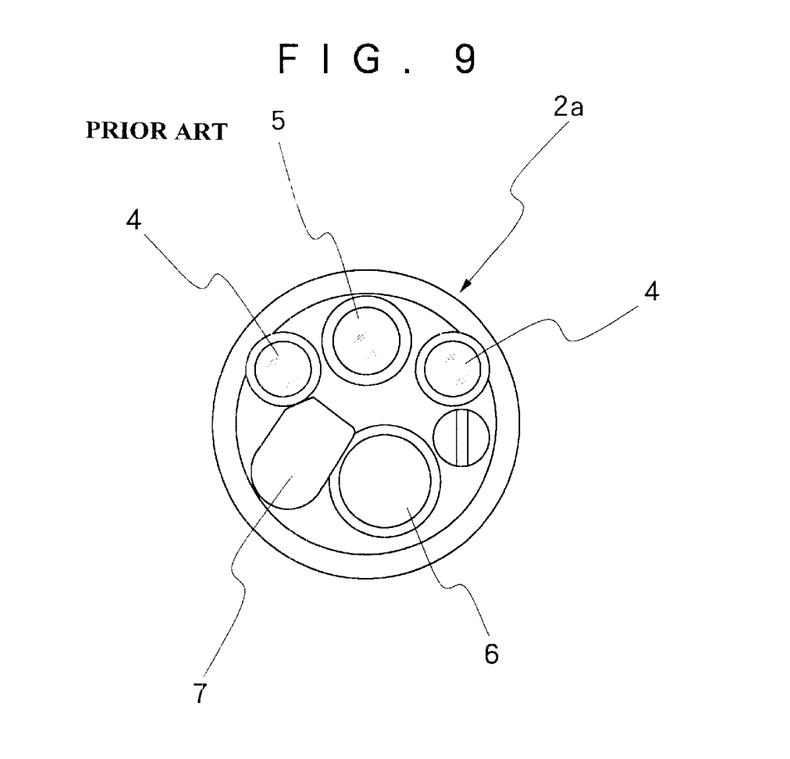
FIG. 9 is an outer view of a fore distal end portion of an insertion instrument of the endoscope shown in FIG. 8.

Firstly, illustrated in FIG. 8 is a general layout of a typical endoscopic insertion instrument in use in medical fields. The endoscopic insertion instrument is largely constituted by a manipulating head assembly 1, a rod-like insert member 2 which is extended out on the front side of the manipulating head assembly 1 for insertion into a body cavity, and a universal cable 3 which is led out on the rear side of the manipulating head assembly 1 for connection to a light source. The insert member 2 comprises at least a rigid tip end section 2a which is internally provided with an observation means, an angle section 2b which is connected to the proximal end of the rigid tip end section 2a, and a lengthy flexible body section 2c which extends from the manipulating head assembly 1 to the proximal end of the angle section. In the case of optical or directly viewing type endoscopes in general, an illumination window or windows 4 and an observation window 5 are provided in a distal end face of the rigid tip end section 2a as shown in FIG. 9 as an endoscopic observation means. The illumination windows 4 are provided for the purpose of projecting illumination light on intracavitary areas under observation, while the observation window 5 is provided for the purpose of observing intracavitary portions of interest therethrough. In addition, endoscopes of this sort are generally arranged to permit insertion of a surgical or therapeutic instrument such as forceps through the insertion instrument as soon as a disorder or a diseased portion is spotted in an intracavitary portion under observation through the observation window. For this purpose, an outlet 6 of a biopsy channel is opened in the distal end face of the rigid tip end section 2a side by side with the illumination and observation windows 4 and 5. Further, a wash nozzle 7 is provided on the rigid tip end section to supply a wash liquid toward the observation window to wash away body fluids or other contaminant liquids therefrom, and then to supply compressed air to dissipate liquid droplets which may remain on the surfaces of the observation window after washing.

Figure 10:
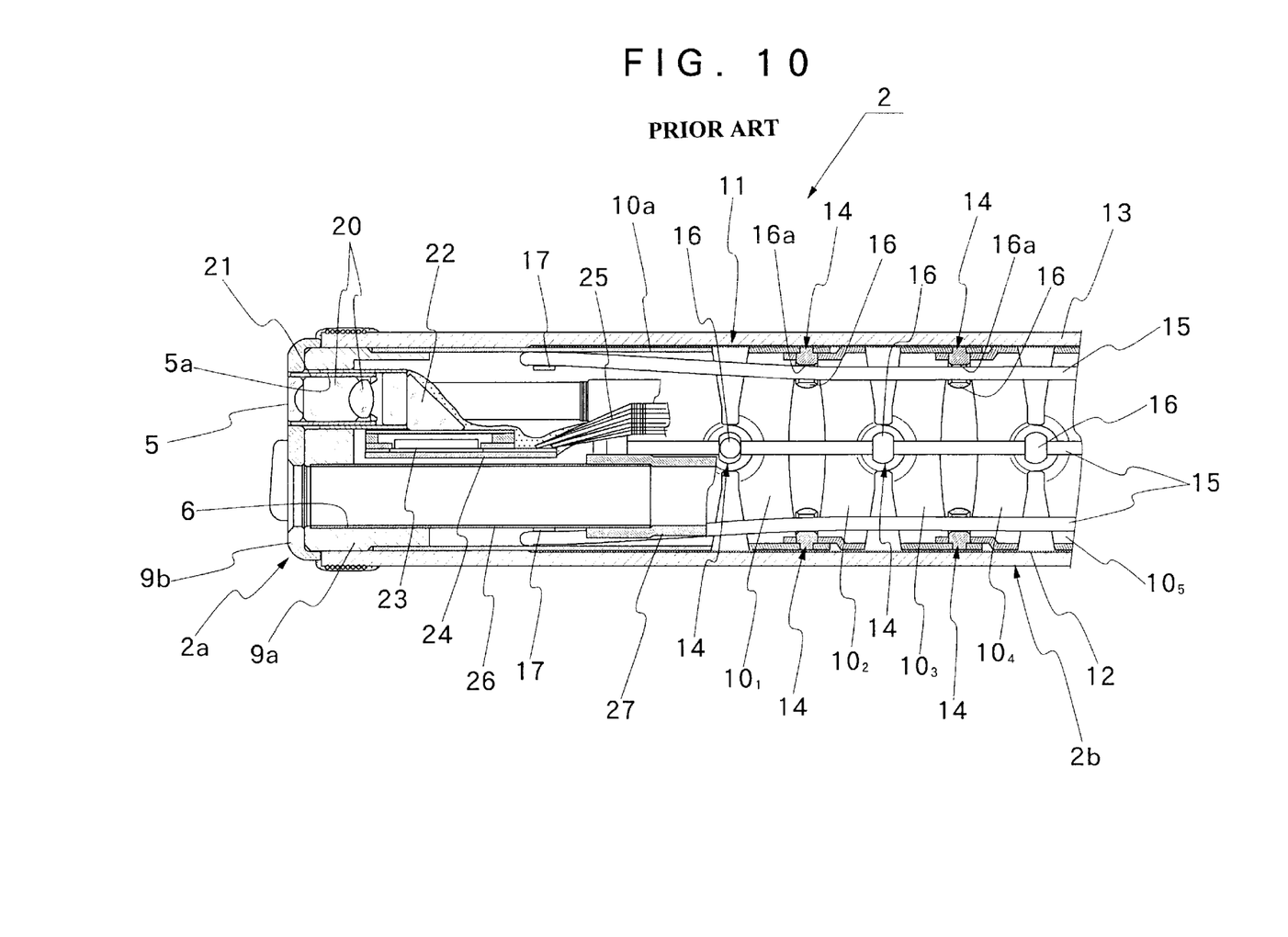
FIG. 10 is a longitudinal section of a prior art endoscopic insertion instrument.

The angle section 2b is generally arranged as shown in FIG. 10. Namely, the angle section 2b is in the form of a flexible tube 11 of a jointed ring structure consisting of a series of pivotally connected angle rings 10. The flexible tube 11 is wrapped in metal wire mesh 12 which is in turn encased in an outer tube forming an outer skin layer 13. The angle rings 10 of the flexible tube 11 includes end rings at the fore and proximal ends to be connected to the rigid tip end section 2a and the flexible body section 2c, respectively, and angle rings which are connected in intermediate positions between the two end rings. FIG. 10 shows a fore end portion of the anglr section 2b.

Indicated at 10a is a front end ring 10a which is fitted in a rigid casing 9a of the rigid tip end section 2a. An insulating cap 9b is fitted on a fore end face of the rigid casing 9a. Accordingly, the fore end 10a constitutes part of a distal rigid section of the insert portion 2. At a proximal end away from the rigid casing 9, the front end ring 10a is provided with a pair of ear portions at the opposite right and left sides thereof, in overlapped relations with ear portions of a first angle ring $10_1$. The overlapped ear portions of the front end ring 10 and the first angle ring $10_1$ are pivotally connected with each other by a pivoting pin 14. These ear portions are formed in a flat plane. At the opposite end away from the front end ring 10a, the first angle ring $10_1$ is provided with axial extensions at the upper and lower sides thereof, in overlapping relations with axial extensions of a second angle ring $10_2$. These overlapped axial extensions are pivotally connected with each other by a pivoting pin 14. In the same manner, the second angle ring $10_2$, third angle ring $10_3$, fourth angle ring $10_4$ and so forth are pivotally connected one after another by means of pivoting pins 14 alternately by way of right and left ear portions and upper and lower axial extensions. Accordingly, two adjacent angle rings which are connected by way of the right and left ear portions are flexible toward and away from each other through a predetermined angle in vertical directions, while two adjacent angle rings which are connected by way of the upper and lower axial extensions are flexible toward and away from each other through a predetermined angle in lateral or rightward and leftward directions. Thus, the flexible tube 11, which is formed by successively connecting a large number of angle rings 10 in the above-described manner, is flexible in upward and downward directions and in rightward and leftward directions as well. Since both of the metal wire mesh 12 and outer skin layer 13 which wrap in the flexible tube 11 are flexible, the angle section 2b can be turned arbitrarily in upward, downward, rightward and leftward directions.

For bending the angle section 2b into a desired direction, an angling knob 8 is provided on the manipulating head assembly 1. For this purpose, a number of operating wires 15 are employed to transmit an operating force from the angling knobs 8 to the angle section 2b. Since the angle section 2b are flexibly bent in four directions, namely, in upward, downward, rightward and leftward directions as mentioned hereinbefore, the operating wires 15 are constituted by four operating wires or two pairs of operating wires, including a first pair of upper and lower operating wires and a second pair of right and left operating wires. At the time of bending the angle section 2b in an upward or downward direction, an operator manipulates the angling knob 8 in such a way as to pull one of the upper and lower operating wires while pushing out the other wire. When bending the angle section 2b rightward or leftward, an operator manipulates the angling knob 8 in such a way as to pull one of the right and left operating wires while pushing out the other wire. By so doing, the angle section 2b is bent in a direction in which a tensile operating force prevails. Further, the upper and lower operating wires can be manipulated in combination with the right and left operating wires to turn the angle section 2b in a twisted form.

Accordingly, within the flexible tube 11, the four operating wires are located strictly in predetermined four separate positions which are shifted from each other by 90 degrees in phase or in the circumferential direction and which are in the close proximity of inner surfaces of the flexible tube 11. Besides, the operating wires 15 should be arranged to be movable smoothly in pushing and pulling directions or in axially in forward and backward directions but should be retained in the respective positions without deviations in radial and circumferential directions. For this purpose, the operating wires 15 are associated with guide means utilizing pivoting pins 14 as shown in FIG. 10.

More specifically, the pivoting pins 14, which function to pivotally connect preceding and succeeding angle rings 10, are each provided with a bulged head portion which is projected radially inward within the flexible tube 11 to serve as a wire guide 16. Each wire guide 16 is bulged in a dome-like shape and provided with a through hole or a wire passage 16a which is bored axially through its dome-like body. The operating wires 14 are slidably threaded respectively through the wire passages of the wire guides 16. In this regard, it has also been known in the art to employ flat-head pivoting pins and to pass the operating wires 14 through lancing arches which are formed in the annular body portions of the angle rings 10. Further, there may be employed guide pins, for example, as disclosed in Japanese Laid-Open Patent Application H3-68326, which are provided with a flange at one end, in addition to an aperture providing a guide passage for an operating wire. In this case, the guide pins are projected into the flexible tube from outside through apertures which are bored at predetermined positions of annular bodies of the angle rings.

Figure 11:
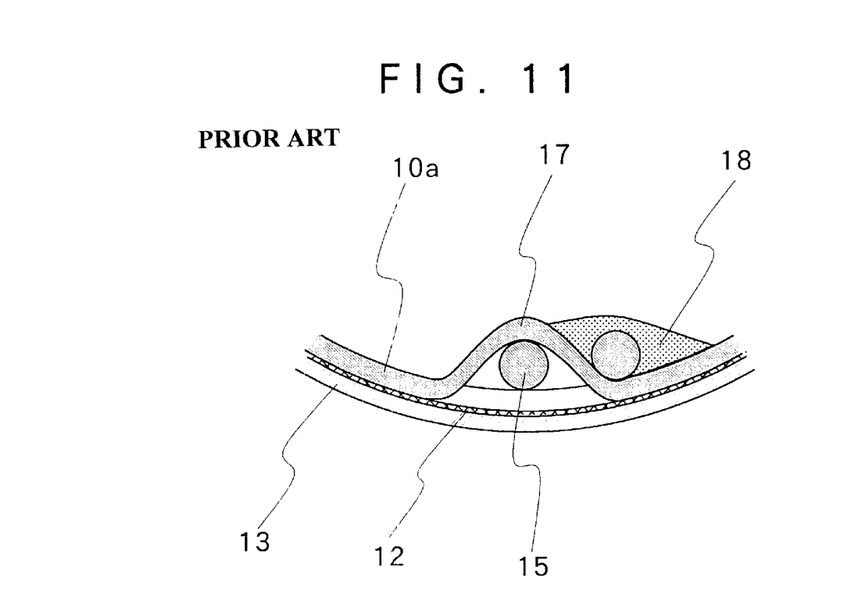
FIG. 11 is a cross-sectional view of one of lancing arches shown in FIG. 10.

In any case, fore ends of the operating wires 15 are fixed either to the front end ring 10a or to the rigid casing 9 of the rigid tip end section. For fixing the fore ends of the operating wires 15, it is the general practice to provide inward lancing arches 17 on the front end ring 10a, passing fore end portions of the operating wires 15 through the lancing arches 17, folding back the passed fore end portions to one side of the lancing arch 17, and fixing the folded fore end portions by soldering 18. Alternatively, after passing a fore end portion of an operating wire through a lancing arch which is provided on the front end ring, a ball-like bulging is formed at the fore end of the operating wire to stop same from coming out of the lancing arch. Further, in some cases, grooves are provided on the outer periphery of the rigid casing, and fore ends of operating wires are fixedly anchored in the grooves by soldering or other means.

Fitted internally of and through the insert member 2 are various components including a light guide which is extended as far as the illumination windows 4, a signal cable from a solid-state image sensor which is located at the focus of an optical objective lens system in the observation window 5 (or an image guide in the case of an optical endoscope), a biopsy channel which is connected to the instrument projecting outlet 6, and a fluid conduit tube which is connected to the washing nozzle 7. All of these components are flexible at least in bending directions, and accordingly are fitted, so to say, in an unfixed state within limited internal spaces of the angle section 2b and the flexible body section 2c without being fixed in particular positions. As seen in FIG. 10, the observation window 5 on the rigid tip end section 2a is constituted by an axial bore 5a, and an optical objective lens system 20 having its lens tube 21 fitted in the axial bore 5a. The optical axis of the objective lens system 20 is bent through 90 degrees by a prism 22 which is located at the rear end of the lens tube 21. As an image pickup means, a solid-state image sensor device 23 is mounted on a substrate circuit board 24 and connected with the prism 22 through a cemented joint. Indicated at 25 is a signal cable which is connected to the substrate wiring board 24 of the solid-state image sensor device 23. Further, the instrument projecting outlet 6 is provided on the rigid tip end section 2a at a position substantially beneath the observation window 5. This instrument projecting outlet 6 is constituted by a passage which is bored axially through the rigid tip end section 2a, and a connector pipe 26 which is fitted in the instrument projecting outlet 6 and projected out of the rigid tip end section 2a by a predetermined length on the side of the angle section 2b. Connected to the projected proximal end of the connector pipe 26 is a fore end of a flexible tube which serves as the biopsy instrument channel 27.

The internal space of the front end ring 10a, which is connected to the rigid casing 9a, forms part of a rigid fore end portion of the insert rod portion 2 and accommodates therein various components, including part of the lens tube 21 and the prism 22 of the endoscopic observation means which is mounted in the rigid tip end section 2a, along with the solid-state image sensor device 23 and its substrate circuit board 24 and the connector pipe 26 of the biopsy instrument channel 27. These components are restricted by the positions of the through bore 5a and the instrument projecting outlet 26 which are provided on the rigid tip end section 2a either to mount the endoscopic observation means or to fit in the connector pipe 26. Further, although not shown in the drawings, the above-mentioned light guide as well as the fluid conduit tube is connected to an aperture hole which is provided on the rigid tip end section 2a through a rigid pipe having a proximal end thereof projected into the internal space of the front end ring 10a.

Within the internal space of the front end ring 10a, a lancing arches 17 and a soldered connection 18 are provided at four different positions for fixing fore ends of the operating wires 15, taking up a relatively large portion of the internal space of the front end ring 10a. On the other hand, positional relations within the front end ring 10a of the respective component parts which are fitted in the insert member 2 are restricted by positions of the illumination and observation windows 4 and 5, instrument projecting outlet 6 and washing nozzle 7, which are located in such positions as would be necessary or at least desirable from the standpoint of operating the endoscope. For instance, it is desirable for the observation window 5 to be located in a position which is as close as possible to a line connecting the upper and lower operating wires 15. On the other hand, it is desirable to locate the illumination windows 15 on the opposite lateral sides of the observation window 5 for the purpose of uniformly illuminating an observation view field. Further, for washing the observation window 5, the position of the washing nozzle 7 is naturally determined and restricted by that function. The instrument projecting outlet 6 should desirably be located in a position which is as close as possible to the observation window 5 and immediately beneath the observation window 5 or as close as possible to a center line of upward and downward bending movements, which connects the upper and lower operating wires 15. However, if the respective components are located in most desirable positions form the standpoint of endoscopic operation, interferences are very likely to occur between these component parts and the lancing arches 17 or the soldered connections 18. Therefore, when laying out the instrument projecting outlet 6 and illumination windows 4 on the basis of a position of the observation window 5, difficulties are usually encountered in locating these parts in most suitable positions.

Regarding the operating wires 15, the distance between the lacing arches 17 and foremost wire guides, through which the operating wires are threaded, remains unchanged, so that this part does not contribute to bending of the angle section 2b to any substantial degree. Accordingly, the positions of the lancing arches 17 can be shifted in the circumferential direction in case they interfere with positions of the instrument projecting outlet 6 and illumination windows 4. However, if the positions of the lancing arches 17 are shifted, the operating wires 15 are bent angularly between the foremost wire guides 16 and the lancing arches 17 and therefore are subjected to larger friction forces within the wire guides 16 each time when the wires 15 in a slackened state are pulled into a tensioned state for an angling operation, making it difficult to move the operating wires 15 smoothly in addition to increased possibilities of damages to the wires 15. In this connection, the angular bending of the operating wires 15 can be moderated by increasing the distance between the foremost wire guides 16 and the lancing arches 17. However, an increase of that distance is inevitably reflected by an increase in length of the rigid portion at the distal end of the insert rod portion 2, which makes it difficult to introduce the endoscope smoothly into a body cavity smoothly and without arousing much pains on the part of a patient.

SUMMARY OF THE INVENTION

With foregoing situations in view, it is an object of the present invention to provide an angling joint tube to be connected to a proximal end of a rigid tip end section of an endoscopic insertion instrument as an angle section, having an operating wire fixation point, which fixedly anchors a fore end of one of operating wires of the angling joint tube, shifted by a predetermined angle from a normal position in the circumferential direction, in combination with a wire guide member which is arranged to minimize a slant angle of the operating wire running toward the angularly shifted wire fixation point.

It is another object of the present invention to provide an angling joint tube of the sort as mentioned above, which permits a greater freedom in laying out various component parts to be fitted into the endoscopic insertion instrument, without necessitating to increase the diameter of the insertion instrument.

It is a further object of the present invention to provide an angling joint tube of the sort as mentioned above, which can prevent interference between a fore fixation point of an operating wire of the angling section and a biopsy channel even in a case an observation window and an instrument projecting outlet of the biopsy channel on a rigid tip end section of the endoscopic insertion instrument are both located in the proximity of a center line of upward and downward bending movements of the rigid tip end section.

According to the present invention, in an endoscopic insertion instrument having a flexibly bendable angle section connected contiguously to a proximal end of a rigid tip end section and adapted to be manipulated through a plural number of operating wires, the angle section including a flexible tube formed by pivotally and successively connecting a plural number of angle rings through pivoting pins, the operating wires being extended axially through the flexible tube via the pivoting pins and having fore ends thereof fixedly anchored at operating wire fixation points in boundary portions between the flexible tube and the rigid tip end section to bend the angling section in an arbitrary direction by pulling or pushing the operating wires, there is provided an angling joint tube for use as an angle section of an endoscopic insertion instrument, which is characterized by the provision of: at least an operating wire fixation point shifted by a predetermined angle in circumferential direction of the flexible tube from a normal position on an axial extension line from a row of pivoting pins to fix at least one operating wire in an angularly shifted position; a wire guide fixedly mounted on a wire guide pin fixedly planted at least on one of angle rings, which are connected by a foremost one in the row of pivoting pins, and arranged to guide the one operating wire in such a way as to evade at least a top portion of the foremost pivoting pin as the operating wire is manipulating in a pulling or pushing direction.

In this instance, it is desirable for a wire guide pin to be provided on each one of the two angle rings which are connected by the foremost pivoting pin which is evaded by the operating wire, and in the same angular positions on the two angle rings in the circumferential direction thereof. In this connection, for ensuring smooth movements of the operating wire and at the same time for protection of the operating wire, the two wire guide pins through which the one operating wire is threaded are preferably welded to the respective angle rings in a tilted state in a direction of moderating a slant angle of the operating wire which is bent toward the angularly shifted wire fixation point.

In routing the operating wires through the angling joint tube, each one of the operating wires can be threaded successively through guide holes of wire guide portions which are provided on the pivoting pins which are arranged in rows in the axial direction to successively connect the angle rings of the flexible tube. In this case, the pivoting pin to be evaded by one operating wire is preferably constituted by a flat-head pivoting pin.

The above and other objects, features and advantages of the present invention will become apparent from the following particular description of the invention, taken in conjunction with the accompanying drawings which show by way of example one preferred embodiment of the invention.

DESCRIPTION OF PREFERRED EMBODIMENTS

Hereafter, the present invention is described more particularly by way of its preferred embodiment shown in the accompanying drawings. In the following description of a preferred embodiment which has no differences in particular from the above-described prior art in basic layout of component parts except layout of a path or paths of an operating wire or wires in the angle portion of the endoscope, those component parts which are equivalent or identical with the counterparts in the above-described prior art are designated by similar reference numerals or characters to avoid repetitions of same explanations.

Figure 1:
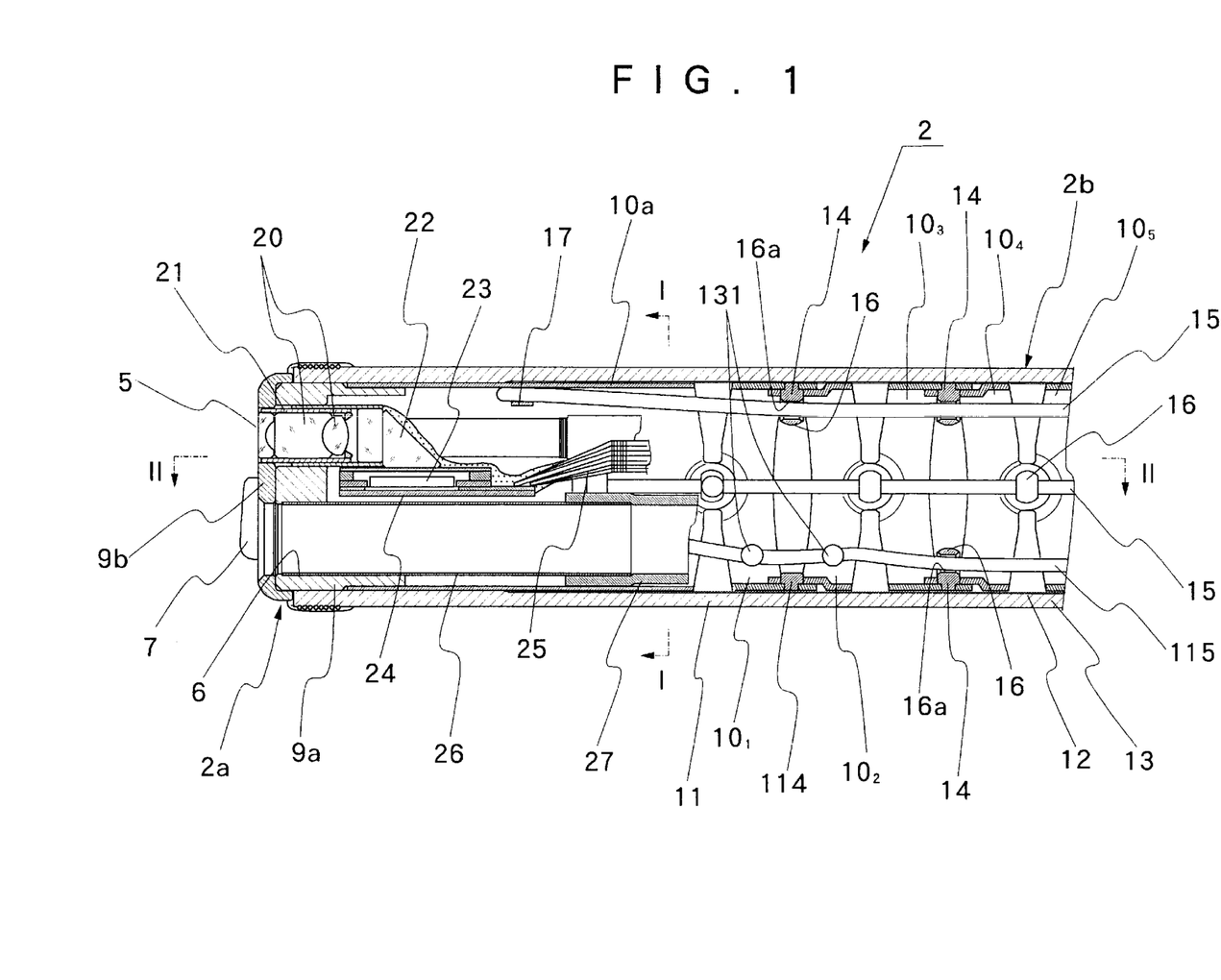
FIG. 1 is a fragmentary longitudinal section through a fore end portion of an endoscopic insertion instrument, including an angle section employing an angling joint tube according to the present invention.
Figure 2:
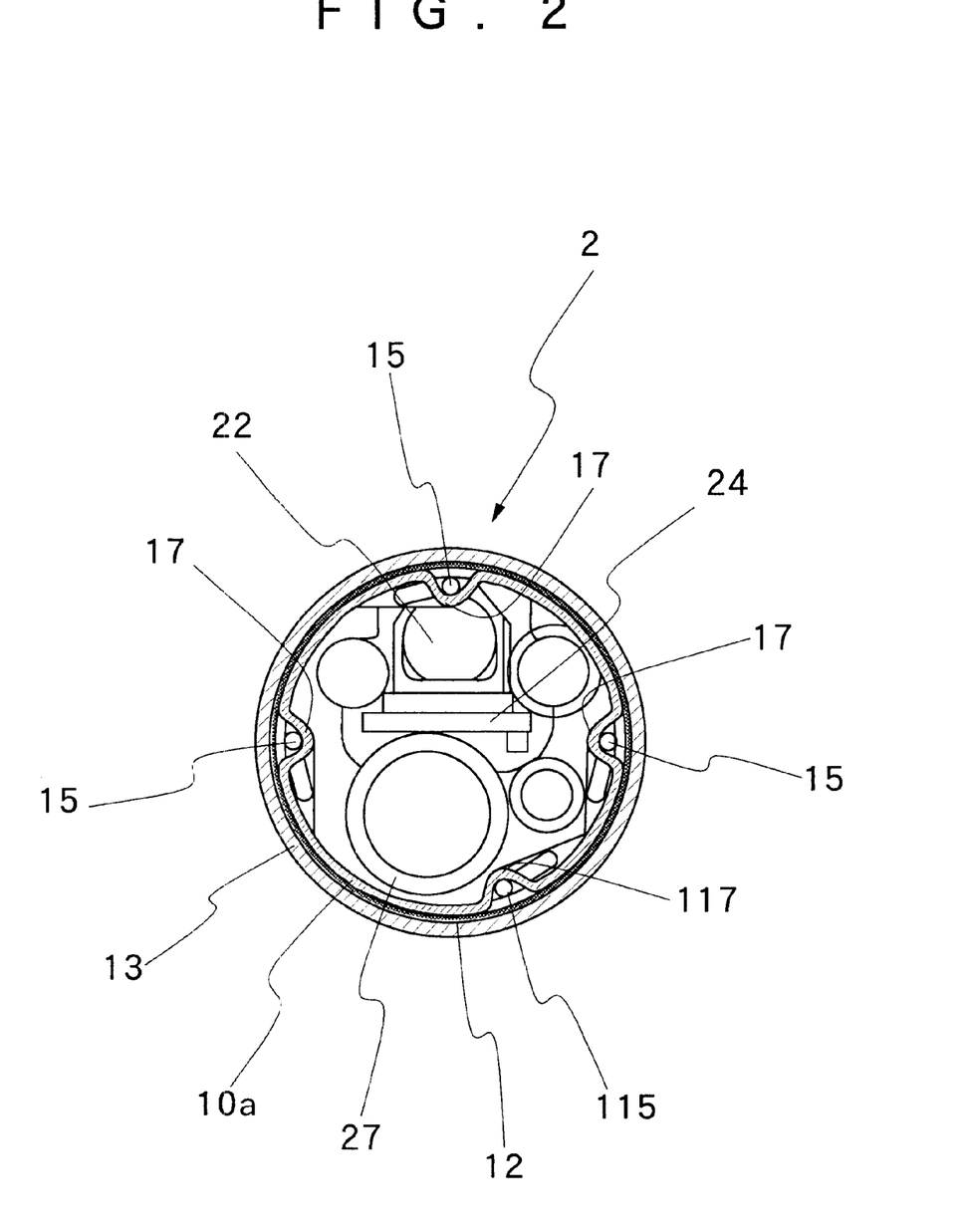
FIG. 2 is a schematic cross section, taken on line II—II in FIG. 1.

As shown in FIGS. 1 and 2, from the standpoint of maneuverability of the endoscope and of biopsy or surgical instruments, a center line of a view field through the observation window 5 on the rigid tip end section 2a should desirably be located on or close to a center line of vertical or upward and downward bending movements, while the instrument projecting outlet 6 should desirably be located immediately beneath the observation window 5 and as close as possible to the center line of the upward and downward bending movements. Provided at a position above the lens tube 21 and prism 22, which are fitted in the observation window, is a lancing arch 17 for fixing an upper operating wire 15 which is pulled at the time of turning the rigid tip end section in an upward direction. Located beneath the lens tube 21 and prism 22 are a connector pipe 26 which is extended rearward from the instrument projecting outlet 6 and a biopsy channel 27 which is in turn fitted on a proximal end of the connector pipe 26, on an axial extension line from a wire guide 16 of a pivoting pin 14 on the front end ring, through which a lower operating wire is threaded as indicated by a reference numeral 115. This lower operating wire 115 is pulled at the time of a downward turning or bending operation.

In the positional relations as described above, a lancing arch 17 which fixedly anchors the fore end of the lower operating wire 115 is provided in a position which is shifted by a predetermined angle in the circumferential direction from a normal position to avoid interference with the instrument projecting outlet 27, that is to say, to make a space for the instrument projecting outlet 27. Accordingly, it becomes possible to set the instrument projecting outlet 27 in a most desirable position on the rigid tip end section 2a. If desired, the top position of the front end ring 10a and/or the position of a lancing arch of a right or left operating wire may be similarly shifted by a certain angle in the circumferential direction, for the purpose of increasing the freedom of layout of the respective internal component parts of the rigid tip end section 2a.

Figure 3:
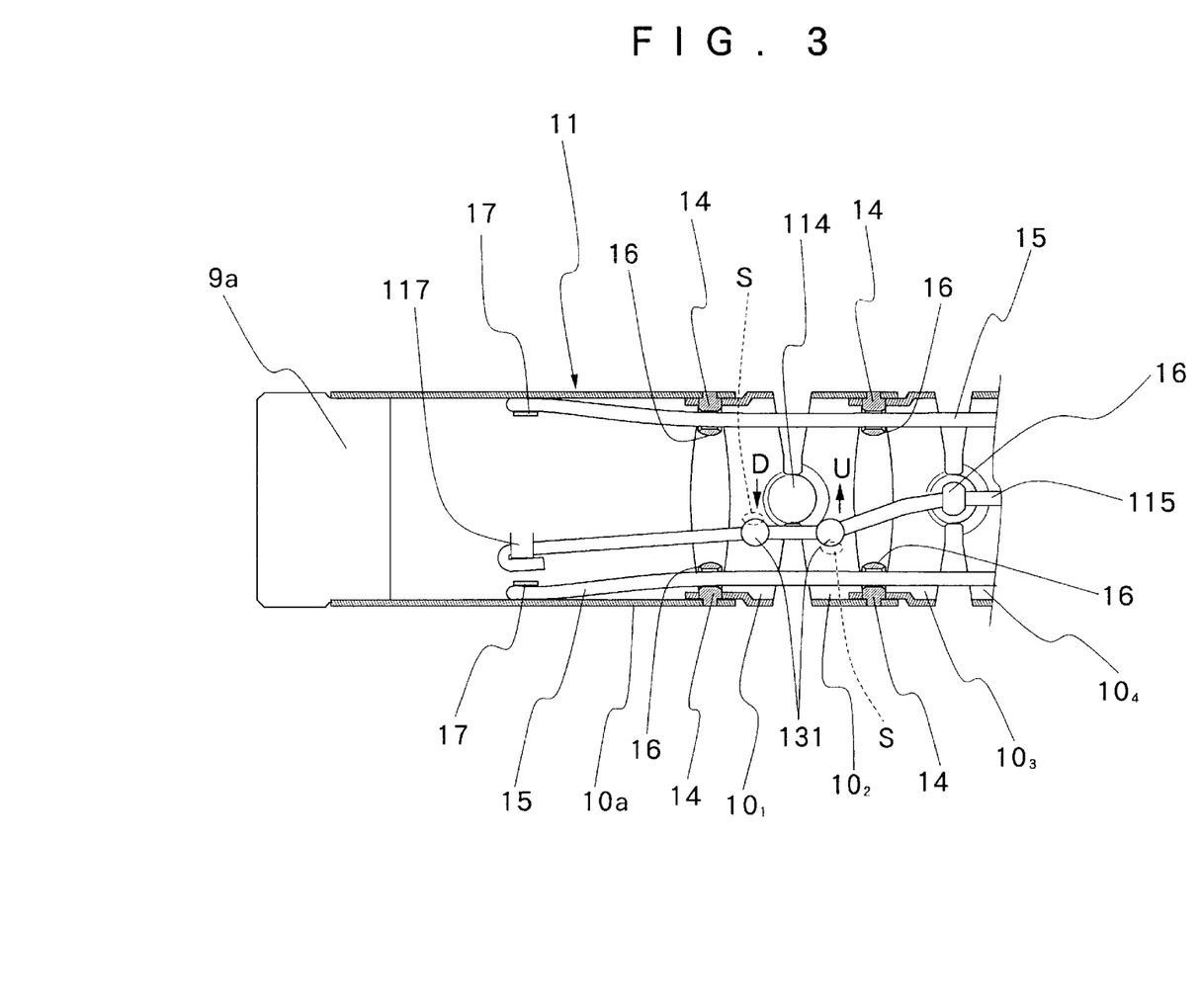
FIG. 3 is a schematic longitudinal section of a flexible tube, taken 18 on line III—III of FIG. 1.

Illustrated in FIG. 3 is an exemplary embodiment in which, of the four operating wires of the endoscope, the position for fixing the fore end of the lower operating wire 115 is shifted from a normal position in the circumferential direction. As seen in that figure, the first angle ring $10_1$, next to the front end ring 10a is pivotally connected to the latter on the opposite right and left sides by means of pivoting pins. At the same time, the first angle ring $10_1$ is pivotally connected to a next or second angle ring $10_2$ on the upper and lower sides thereof. Similarly, the second angle ring $10_2$ is pivotally connected to a next or third angle ring $10_3$ on the right and left sides, the third angle ring $10_3$ is pivotally connected to a next or fourth angle ring $10_4$ on the upper and lower sides, and the fourth angle ring $10_4$ is pivotally connected to a next or fifth angle ring 105 on the right and left sides thereof.

At the proximal end of the angle section 2b which is connected to the flexible body section 2c, more particularly, at the point of pivotal connection between the third and fourth angle rings $10_3$ and $10_4$ which are pivotally connected with each other by a pivoting pin 14 with a wire guide 16, the lower operating wire 115 is threaded through a wire passage hole 16a of the wire guide 16. However, as indicated at 114, the first and second angle rings $10_1$ and $10_2$ are connected by a flat pivoting pin without a wire guide. Therefore, the operating wire 115 is bypassed by the flat pivoting pin 114 and threaded through a lancing arch 117 which is provided on the front end ring 10a at a radially shifted position relative to an axial extension line from the pivoting pin 14. This arrangement permits to increase the length of that part of the operating wire 115 which is angularly bent in the circumferential direction, that is to say, to moderate the bending angle of the operating wire 115. Namely, an angular shift in the circumferential direction of the position of the lancing arch 117 can be absorbed to some extent between the lancing arch 117 and the pivoting pin 14 which pivotally connects the fourth and fifth angle rings $10_4$ and $10_5$.

Further, the flat pivoting pin 114, which is provided with no wire guide and therefore bypassed by the operating wire 115, is projected from the inner peripheral surface of the flexible tube 11. Accordingly, it is necessary to prevent the operating wire 115 from entangling around the pivoting pin 114 or colliding against and riding over the large diameter portion 114a of the pivoting pin 114 at the time when the operating wire 115 is deflected in a lateral direction, namely, at the time when the operating wire 114 in a slackened state in a meandering shape is tensioned by a pull or at the time of a compound bending operation using the upper and lower operating wires in combination with the right and left operating wires.

Figure 4:
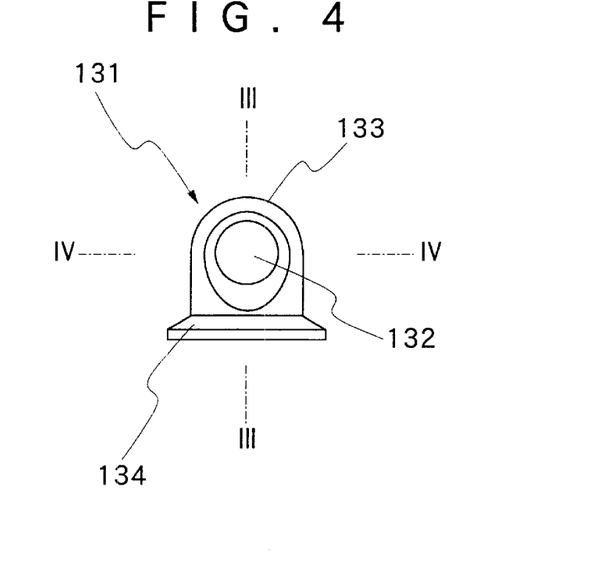
FIG. 4 is a schematic front view of a wire guide pin.
Figure 5:
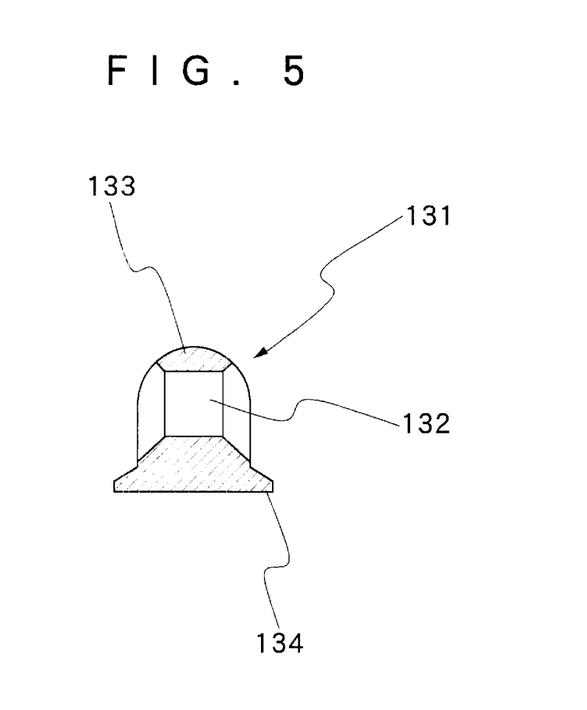
FIG. 5 is a schematic sectional view, taken on line V—V of FIG. 4.
Figure 6:
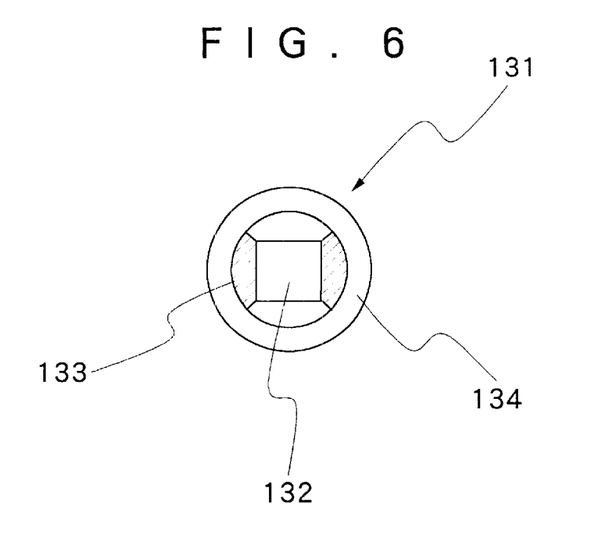
FIG. 6 is a schematic sectional view, taken on line VI—VI of FIG. 4.

To this end, the operating wire 115 is guided in such a way as to dodge the flat pivoting pin 114. More specifically, a wire guide pin 131 is planted in an aperture which is bored in the annular body portion of each one of the first and second angle rings $10_1$ and $10_2$ which are connected by the flat pivoting pin 114, at a position approximately intermediate between the pivoting pin 114 and the lancing arch 117. As shown in FIGS. 4 to 6, these guide pins 131 are each constituted by a main body 133 with a guide hole 132 which is diverged toward the opposite ends thereof, and a stopper flange 134 which is provided at outer end of the main body 133. The aperture which is provided in the angle pin for mounting the wire guide pin 131 is formed in an diameter which is larger than the outside diameter of the main body 133 of the wire guide pin 131 but smaller than the flange 134. Thus, the wire guide pins 131 can be inserted into the flexible tube from outside the angle rings 10a and 102 such that the respective wire passage holes 132 lie in the axial direction of the angle section 2b, and fixed in position from outside by spot welding.

By fixing the wire guide pins 131 to the angle rings $10_1$ and $10_2$ by spot welding as described above, it becomes possible to omit a post-fixation treatment such as a washing treatment which would become necessary in case the wire guide pins are fixed by soldering or the like. Besides, if desired, dummy operating wires may be threaded through the wire passage holes 132 of the wire guide pins 131 before spot welding the latter to the angle rings. In such a case, by connecting the operating wires 115 to the dummy wires and then pulling out the dummy wires, the operating wires 115 can be smoothly threaded through the wire passage holes 132 of the wire guide pins 131 despite the positions of the wire guide pins 131 are shifted in the circumferential direction as compared with the wire guides 16 on the pivoting pins 14.

In the manner as described above, after being threaded through a wire passage hole 16a of a wire guide 16 on a pivoting pin 14 which connects the third and fourth angle rings $10_3$ and $10_4$, the operating wire 115 is passed successively through the wire guide pins 131 which are provided on the angle rings $10_2$ and $10_1$, and then the fore end of the operating wire 115 is threaded through the lancing arch 117 and folded back and fixed by soldering. Thus, the operating wire 115 is routed completely clear of the flat pivoting pin 114, being guided angularly relative to the longitudinal axis of the angling section 2b between the pivoting pin 14 and the wire guide pin 131 on the second angle ring $10_2$ and parallel with the longitudinal axis between the two wire guide pins 131. From the wire guide pin 131 on the first angle ring $10_1$ to the lancing arch 117, the operating wire 115 is guided angularly again relative to the longitudinal axis of the angling section 2b.

At the interval between the second angle ring $10_2$ and the third angle ring $10_3$, the operating wire 115 is guided in a rectilinear form so that a pulling force on the operating wire 115 acts to reduce the breadth of the interval, permitting to apply a bending force to the second and third angle rings $10_2$ and $10_3$ in a reliable manner and with a smaller load. Accordingly, the operating wire 115 can be manipulated smoothly at the time of bending the angling section 2b downward. Besides, since the operating wire 115 is guided to evade the flat pivoting pin 114 in an assured manner as described above, it can be retained out of contact with the flat pivoting pin 114 at the time of pushing and pulling operations.

Figure 7:
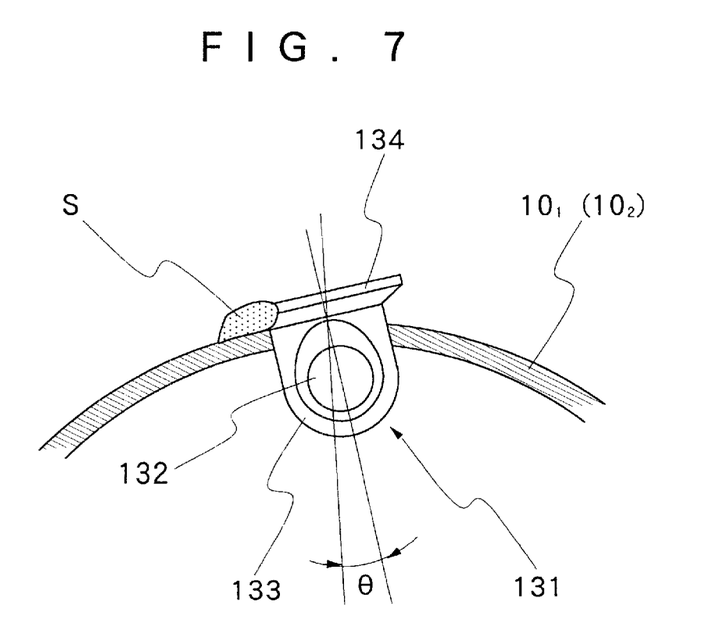
FIG. 7 is a schematic view of a wire guide pin fixedly anchored in an angle ring.

In this instance, as a result of location of the lancing arch 117 in an angularly shifted position, the operating wire 115 is slanted from the longitudinal axis of the angling section 2b, starting from the pivoting pin 14 between the third and fourth angle rings $10_3$ and $10_4$. In this regard, actually the distance of this slant section can be made large enough for minimizing the slant angle of the operating wire 115. In order to further reduce the slant angle of the operating wire 115 for ensuring its smooth movements, the wire guide pins 131 can be fixed to the angle rings $10_1$ and $10_2$ in an inclined state as shown in FIG. 7. This can be done by spot-welding a circumferential portion of the stopper flange 134 as indicated at S. By so doing, the flange 134 as a whole can be fixed to the outer peripheral surface of the angle ring in an inclined state.

As shown in FIG. 3, the main body 133 of the wire guide pin 131 on the angle ring $10_1$ is tilted in the direction of arrow D thereby to moderate the slant angle of the operating wire 115 between the wire guide pin 131 to the lancing arch 117. On the other hand, the wire guide pin 131 on the angle ring $10_2$ is tilted inversely in the direction of arrow U to moderate the slant angle of the operating wire 115 between the wire guide pin 131 and the wire guide 16 on the pivoting pin 14. These arrangements contribute to make the movements of the operating wire 115 smooth at the time of bending the angling section 2b in a downward direction, and to lessen the load of operation.

As a guide member for threading an operating wire at a predetermined radial position within the flexible tube of the angling section, a lancing arch may be formed in the annular body portion of the angle ring in place of the above-described pivoting pin with a wire guide portion if desired.

What is claimed is:

1. In an endoscopic insertion instrument, having an angle section connected contiguously to a proximal end of a rigid tip end section thereof and adapted to be manipulated through a plural number of operating wires, said angling section including a flexible tube formed by pivotally and successively connecting a plural number of angle rings through pivoting pins, said operating wires being extended axially through said flexible tube via said pivoting pins and having fore ends thereof fixedly anchored at operating wire fixation points in boundary portions between said flexible tube and said rigid tip end section to bend said angling section in an arbitrary direction by pulling or pushing said operating wires, an angling joint tube for said angle section of said endoscopic insertion instrument, comprising:
at least an operating wire fixation point shifted by a predetermined angle in circumferential direction of said flexible tube from a normal position on an axial extension line from a row of pivoting pins to fix at least one operating wire in an angularly shifted position;
a wire guide fixedly mounted on a wire guide pin fixedly planted at least on one of angle rings, which are connected by a foremost one in said row of pivoting pins, and arranged to guide said one operating wire in such a way as to evade at least a top portion of said foremost pivoting pin as said operating wire is manipulating in a pulling or pushing direction.

2. An angling joint tube as defined in claim 1, wherein said wire guide pin is fixedly provided on each one of preceding and succeeding angle rings connected by said foremost pivoting pin, said wire guide pins being located substantially in the same angular positions in the circumferential direction.

3. An angling joint tube as defined in claim 1, wherein said operating wires are threaded through wire guide holes provided in bulged head portions of said pivoting pins except said foremost pivoting pin evaded by said one operating wire, said foremost pivoting pin being constituted by a flat-head pivoting pin.

4. An angling joint tube as defined in claim 1, wherein said wire guide pin is constituted by a stud-like main body with a wire threading hole and a stopper flange provided at one end of said main body, and inserted into said angle ring from outside through an aperture provided in the latter.

5. An angling joint tube as defined in claim 4, wherein said wire guide pin, having said one operating wire threaded therethrough, is fixedly welded to said angle ring in a tilted state to moderate a bending angle of said one operating wire extending toward angularly shifted fixation point.

* * * * *